United States Patent [19]

Smith et al.

[11] 4,431,645
[45] Feb. 14, 1984

[54] ANTIHYPERTENSIVE AGENTS

[75] Inventors: Elizabeth M. Smith, Verona; Joseph T. Witkowski, Morris Township, Morris County, both of N.J.

[73] Assignee: Schering Corporation, Kenilworth, N.J.

[21] Appl. No.: 355,639

[22] Filed: Mar. 8, 1982

[51] Int. Cl.³ ............... C07D 285/24; C07D 417/12; A61K 31/40; A61K 31/54
[52] U.S. Cl. ........................... 424/246; 424/274; 544/13; 548/452; 548/533
[58] Field of Search ............... 544/13; 424/246, 274; 548/452, 533

[56] References Cited

U.S. PATENT DOCUMENTS 3,110,716 11/1963 McLamore et al. ............... 544/13

FOREIGN PATENT DOCUMENTS 2073187 10/1981 United Kingdom .

OTHER PUBLICATIONS

Cuttings Handbook of Pharmacology, 6th Ed., Chapter 20, pp. 190–195.

*Primary Examiner*—John M. Ford
*Attorney, Agent, or Firm*—Anita W. Magatti; Bruce M. Eisen

[57] ABSTRACT

Compounds of the formula

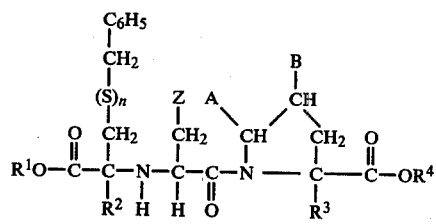

and the pharmaceutically acceptable salts thereof, wherein $R^1$, $R^2$, $R^3$ and $R^4$ are independently selected from hydrogen or lower alkyl; n is 1 or 0; A and B taken together with the carbons to which they are attached form an alkylene ring having six carbon atoms or A and B are hydrogen; and Z is

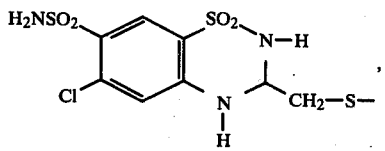

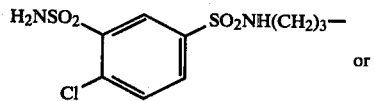

or

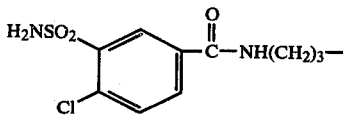

The compounds are useful as hypertensive agents.

17 Claims, No Drawings

ANTIHYPERTENSIVE AGENTS

The present invention relates to carboxyalkyl dipeptides substituted with a benzothiadiazine group, a sulfamoylarenesulfonamido group, or a sulfamoylarene carboxamido group. The compounds are useful as antihypertensive agents.

The compounds of the present invention may be represented by the formula

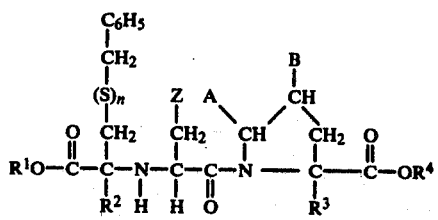

and the pharmaceutically acceptable salts thereof, wherein $R^1$, $R^2$, $R^3$ and $R^4$ are independently selected from hydrogen or lower alkyl; n is 1 or 0; A and B taken together with the carbons to which they are attached form an alkylene ring having six carbon atoms or A and B are hydrogen; and Z is

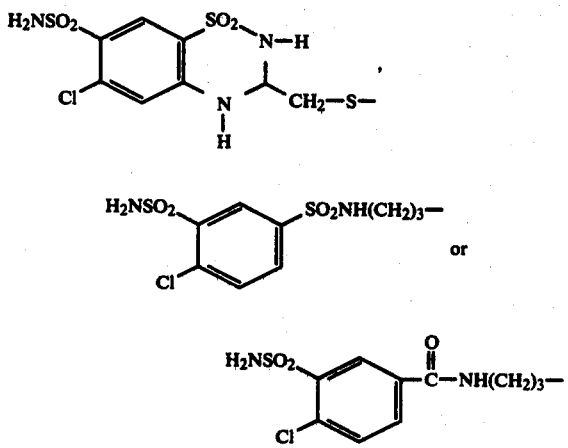

One aspect of the present invention comprises compounds of the formula

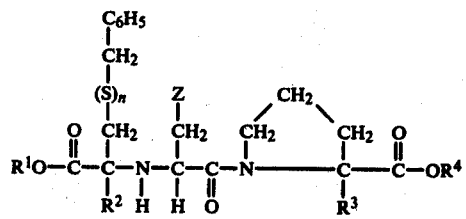

wherein $R^1$, $R^2$, $R^3$, $R^4$ n and Z are as defined above.

A second aspect of the present invention comprises compounds of the formula

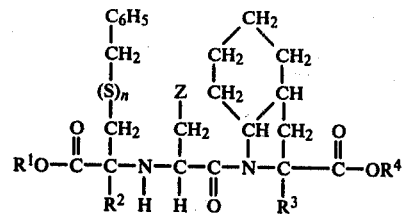

wherein $R^1$, $R^2$, $R^3$, $R^4$, n and Z are as defined above.

One embodiment of the present invention comprises compounds of the formula

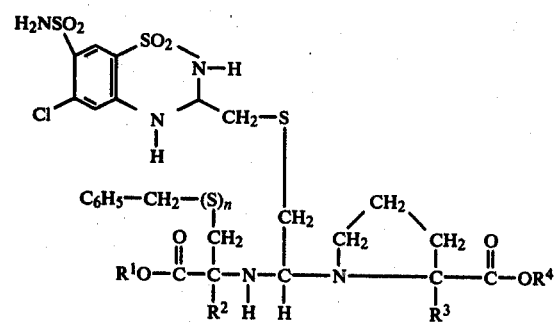

and the pharmaceutically acceptable salts thereof, wherein $R^1$, $R^2$, $R^3$, $R^4$ and n are as defined above.

Another embodiment of the present invention comprises compounds of the formula

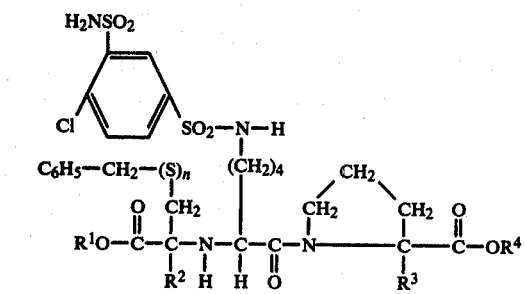

and the pharmaceutically acceptable salts thereof, wherein $R^1$, $R^2$, $R^3$, $R^4$ and n are as defined above.

Another embodiment of the present invention comprises compounds of the formula

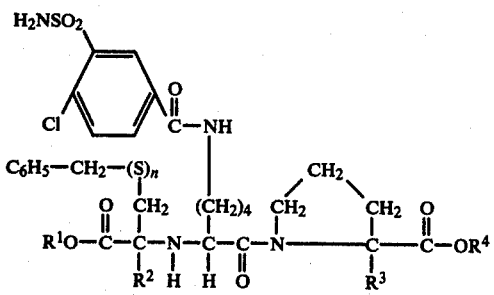

and the pharmaceutically acceptable salts thereof, wherein $R^1$, $R^2$, $R^3$, $R^4$ and n are defined above.

Another embodiment of the present invention comprises compounds of the formula

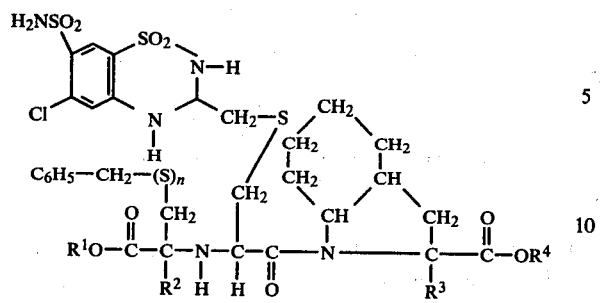

and the pharmaceutically acceptable salts thereof, wherein R, $R^1$, $R^2$, $R^3$, $R^4$ and n are as defined above.

Another embodiment of the present invention comprises compounds of the formula

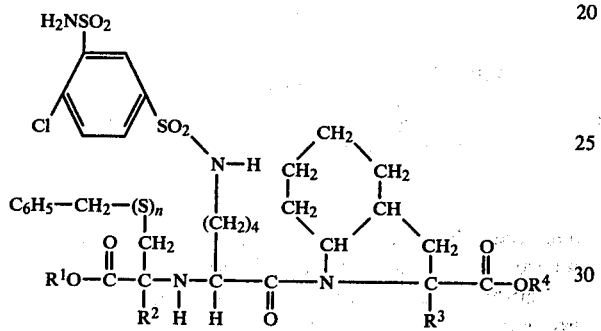

and the pharmaceutically acceptable salts thereof, wherein $R^1$, $R^2$, $R^3$, $R^4$ and n are as defined above.

Another embodiment of the present invention comprises compounds of the formula

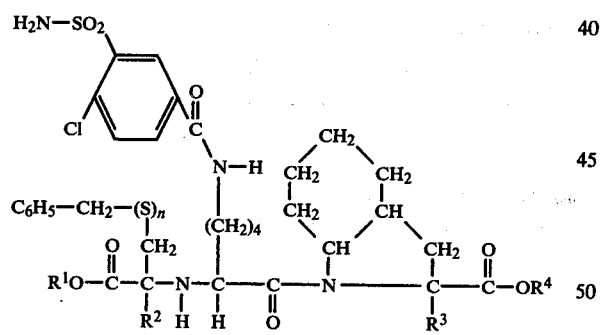

and the pharmaceutically acceptable salts thereof, wherein $R^1$, $R^2$, $R^3$, $R^4$ and n are as defined above.

The aforementioned compounds of the formula I, as defined above, include various stereoisomers. Preferred stereoisomers are those in which the configurations adjacent to the nitrogen atoms correspond most closely to natural L-aminoacids. The lower alkyl groups, except where noted otherwise, include straight and branched chain hydrocarbon radicals from one to six carbon atoms, for example, methyl, ethyl, propyl, isopropyl, butyl, isobutyl, t-butyl, pentyl, isopentyl, hexyl or vinyl, allyl, butenyl and the like.

Compounds of the present invention may be prepared as follows:

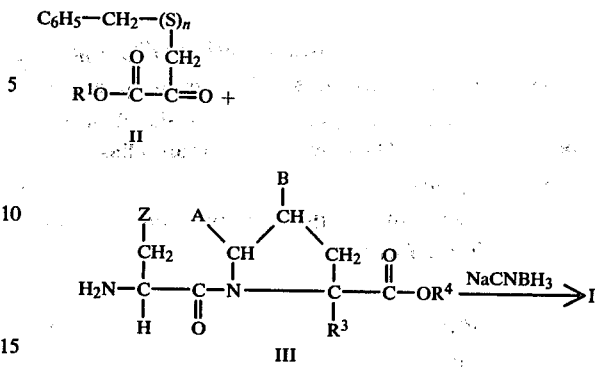

Keto acid (or ester) II is condensed with dipeptide III in aqueous solution, optimally near neutrality, or in a suitable organic solvent (for example, $CH_3OH$) in the presence of sodium cyanoborohydride to give I. Alternatively, the intermediate Schiff base, enamine, or aminol may be catalytically reduced to yield product I, for example, by hydrogen in the presence of 10% palladium on carbon or of Raney nickel. The ratio of diasteriomeric products formed may be altered by choice of catalyst.

If $R^1O$ is a carboxy protecting group such as alkoxy or benzyloxy, it can be converted by well known methods such as hydrolysis or hydrogenation to I, wherein $R^1O$ is hydroxy. This is also the case in all of the methods referred to below.

Alternatively, II can be condensed with aminoacid IV under the same conditions to yield aminoacid V:

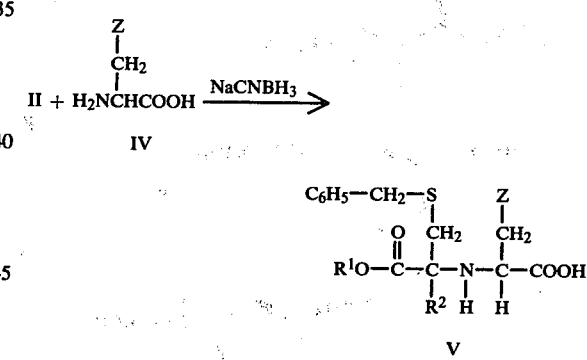

Subsequent coupling by known methods with amino acid derivative VI gives I

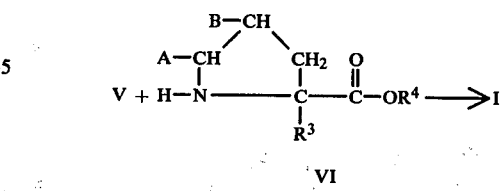

The known methods encompass reactive group protection during the coupling reaction, for example, by N-formyl, N-t-butoxycarbonyl and N-carbobenzyloxy groups followed by their removal to yield I. Furthermore, the carboxylic acid function in VI may be protected by removable ester groups such as benzyl, ethyl, t-butyl, and the like. Condensing agents in this synthetic route are typically those useful in peptide chemistry.

Compounds V or I where Z is (CH$_2$)$_3$NH$_2$ can be coupled with the appropriately substituted aroyl chloride or arenesulfonyl chloride in a suitable solvent (e.g. THF or pyridine) to form the respective amide or sulfonamide bond.

Compounds V or I where Z is CH$_2$SCH$_2$C$_6$H$_5$ can be reduced with sodium in liquid ammonia, followed by coupling with a 3-halomethylbenzothiadiazine in a suitable solvent (e.g. DMF) to give V or I where Z is

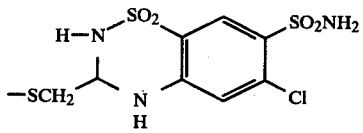

Included among the compounds of the present invention are the following:

1-{Nα-[1(S)-Ethoxycarbonyl-3-phenylpropyl]-Nε-[(4-chloro-3-sulfamoyl)benzenesulfonyl]-(S)-lysyl}-cis,-syn-octahydro-1H-indole-2-(S)-carboxylic acid;

1-{Nα-[1(S)-Ethoxycarbonyl-3-phenylpropyl]-Nε-[(4-chloro-3-sulfamoyl)benzoyl]-(S)-lysyl}-cis,syn-octahydro-1H-indole-2-(S)-carboxylic acid;

1-{Nα-[1(S)-Ethoxycarbonyl-3-phenylpropyl]-Nε-[(4-chloro-3-sulfamoyl)benzenesulfonyl]-(S)-lysyl}-(S)-proline;

1-{Nα-[1(S)-Ethoxycarbonyl-3-phenylpropyl]-Nε-[(4-chloro-3-sulfamoyl)benzoyl]-(S)-lysyl}-(S)-proline;

1-{Nα-[1(S)-Carboxy-3-phenylpropyl]-Nε-[(4-chloro-3-sulfamoyl)benzenesulfonyl]-(S)-lysyl}-cis,syn-octahydro-1H-indole-2-(S)-carboxylic acid;

1-{Nα-[1(S)-Carboxy-3-phenylpropyl]-Nε-[(4-chloro-3-sulfamoyl)benzenesulfonyl]-(S)-lysyl}-(S)-proline;

1-{Nα-[1(S)-Carboxy-3-phenylpropyl]-Nε-[(4-chloro-3-sulfamoyl)benzoyl]-(S)-lysyl}-cis,syn-octahydro-1H-indole-2-(S)-carboxylic acid;

1-{Nα-[1-(S)-Carboxy-3-phenylpropyl]-Nε-[(4-chloro-3-sulfamoyl)benzoyl]-(S)-lysyl}-(S)-proline;

1-{N-[1(S)-Carboxy-3-phenylpropyl]-S-[3-(6-chloro-3,4-dihydro-7-sulfamoyl-1,2,4-benzothiadiazinyl-1,1-dioxide)-methyl]-(R)-cysteinyl}-cis,syn-octahydro-1H-indole-2-(S)-carboxylic acid;

1-{N-[1(S)-Ethoxycarbonyl-3-phenylpropyl]-S-[3-(6-chloro-3,4-dihydro-7-sulfamoyl-1,2,4-benzothiadiazinyl-1-1-dioxide)-methyl]-(R)-cysteinyl}-cis,syn-octahydro-1H-indole-2-(S)carboxylic acid;

1-{N-[1(S)-Carboxy-3-phenylpropyl]-S-[3-(6-chloro-3,4-dihydro-7-sulfamoyl-1,2,4-benzothiadiazinyl-1,1-dioxide)methyl]-(R)-cysteinyl}-(S)-proline;

1-{N-[1(S)-Ethoxycarbonyl-3-phenylpropyl]-S-[3-(6-chloro-3,4-dihydro-7-sulfamoyl-1,2,4-benzothiadiazinyl-1,1-dioxide)methyl]-(R)-cysteinyl}-(S)-proline;

1-{Nα-[1(R)-(Ethoxycarbonyl)-2-(benzylthio)ethyl]-Nε-[(4-chloro-3-sulfamoyl)benzoyl]-(S)-lysyl}-cis,-syn-octahydro-1H-indole-2-(S)-carboxylic acid;

1-{Nα-[1(R)-(Ethoxycarbonyl)-2-(benzylthio)ethyl]-Nε-[4-chloro-3-sulfamoyl)benzenesulfonyl]-(S)-lysyl}-cis,syn-octahydro-1H-indole-2-(S)-carboxylic acid;

1-{N-[1(R)-(Ethoxycarbonyl)-2-(benzylthio)ethyl]-S-[3-(6-chloro-3,4-dihydro-7-sulfamoyl-1,2,4-benzothiadiazinyl-1,1-dioxide)methyl]-(R)-cysteinyl}-cis,-syn-octahydro-1H-indole-2-(S)-carboxylic acid;

1-{Nα-[1(R)-(Carboxy)-2-(benzylthio)ethyl]-Nε-[4-chloro-3-sulfamoyl)benzoyl]-(S)-lysyl}-cis,syn-octahydro-1H-indole-2-(S)-carboxylic acid;

1-{Nα-[1(R)-(Carboxy)-2-(benzylthio)ethyl]-Nε-[4-chloro-3-sulfamoyl)benzenesulfonyl]-(S)-lysyl}-cis,-syn-octahydro-1H-indole-2-(S)-carboxylic acid;

1-{Nα-[1(S)-Ethoxycarbonyl-3-phenylpropyl]-Nε-[(4-chloro-3-sulfamoyl)benzenesulfonyl]-(S)-lysyl}-cis,-syn-octahydro-1H-indole-2-(S)-carboxylic acid, ethyl ester;

1-{Nα-[1(S)-Ethoxycarbonyl-3-phenylpropyl]-Nε-[(4-chloro-3-sulfamoyl)benzoyl]-(S)-lysyl}-cis,syn-octahydro-1H-indole-2-(S)-carboxylic acid, ethyl ester; and 1-{N-[1(R)-Ethoxycarbonyl-3-phenylpropyl]-S-[(3-(6-chloro-3,4-dihydro-7-sulfamoyl-1,2,4-benzothiadiazinyl-1,1-dioxide)-methyl]-(R)cysteinyl}-cis,syn-octahydro-1H-indole-2-(S)-carboxylic acid, ethyl ester.

EXAMPLE 1

1-{Nα-[1(S)-Ethoxycarbonyl-3-phenylpropyl]-(S)-lysyl}-cis,syn-octahydro-1H-indole-2-(S)-carboxylic acid A. Stir a suspension of 24.0 g of Nε-benzyloxycarbonyl-(S)-lysine and 36.0 g of ethyl 2-oxo-4-phenylbutanoate acid in 2500 ml of absolute ethanol at room temperature for 24 hours. Add 16.0 g of sodium cyanoborohydride and stir the resulting mixture at room temperature for 48 hours. Add 80 ml of water and stir the resulting mixture at room temperature for 72 hours. Concentrate this mixture in vacuo at 30° C. to give a white residue. Suspend the residue in 1200 ml of ice water, add concentrated hydrochloric acid to maintain pH 2–4, and stir this mixture for 2 hours. Absorb this aqueous solution on 2000 ml of XAD-2 (Rohm & Hass Co.) resin. Elute the resin with 16,000 ml of water and then with 8000 ml of absolute ethanol. Concentrate the ethanol solution and chromatograph the residue on a column of silica gel (3000 ml, 60–200 mesh) eluting with chloroform:isopropanol:7% ammonium hydroxide 1:1:1 (organic layer) to give a white residue. Chromatograph this residue on a column of silica gel (3000 ml), eluting with chloroform:isopropanol:7% ammonium hydroxide 1:1:1 (organic layer) to give fractions A, B, C, and D. Absorb fraction B on a column of silica gel (1500 ml), eluting with chloroform:isopropanol:7% ammonium hydroxide 1:1:1 (organic layer) to give N-benzyloxycarbonyl-Nα-[1(S)-carboethoxy-3-(phenyl)propyl]-(S)-lysine, a white solid, $[\alpha]_D^{26}$+6.1° (ethanol), m.p. 114°–115° C.

B. Cool a solution of 1.9 g of the product of part A and 1.3 g of cis,syn-octahydro-1H-indole-2-(S)-carboxylic acid benzyl ester in 24 ml of dimethylformamide to 0° C. under nitrogen. Add dropwise a solution of 0.9 of diphenylphosphorylazide in 6 ml of dimethylformamide, followed by a solution of 0.7 ml of N-methylmorpholine in 6 ml of dimethylformamide, also added dropwise, and stir at room temperature for 18 hours. Pour the reaction solution into water, adjust to pH 8 with 1 N, NaOH, and extract with ether. Dry the ether layer over magnesium sulfate, and concentrate under vacuum to a yellow oil. Chromatograph the oil on silica gel (1000 ml, 60–200 mesh), eluting with hexane:ethyl acetate (1:2) to give 1-{Nα-[1(S)-carboethoxy-3-(phenyl)propyl]-Nε-benzyloxycarbonyl-(S)-lysyl}-cis,syn-octahydro-1H-indole-2(S)-carboxylic acid, benzyl ester, a yellow oil.

C. Dissolve 1.60 g of the product of part B in 150 ml of absolute ethanol. Add 0.75 g of 10% palladium-oncharcoal and hydrogenate the mixture at 50 psi at room temperature. Filter the reaction mixture and concentrate the filtrate in vacuo to give 1-{Nα-[1(S)-ethoxycarbonyl-3-(phenyl)-propyl]-(S)-lysyl}-cis,syn-octahydro-1H-indole-2(S)-carboxylic acid hydrate, a white foam, $[\alpha]_D^{26} -42.5$ (ethanol).

EXAMPLE 2

1-{Nα-[1-(S)-Ethoxycarbonyl-3-phenylpropyl]-Nε-[(4-chloro-3-sulfamoyl)benzenesulfonyl]-(S)-lysyl}-cis,syn-octahydro-1H-indole-2(S)-carboxylic acid To 4.9 g of 1-{Nα-[1(S)-[ethoxycarbonyl-3-phenylpropyl]-(S)-lysyl}-cis,syn octahydro-1H-indole-2(S)-carboxylic acid in 200 ml of tetrahydrofuran and 2 g of triethylamine at 0°–5° C., add 2.9 g of 4-chloro-3-sulfamoylbenzenesulfonyl chloride and stir the resulting mixture at room temperature. Concentrate the resulting mixture in vacuo and chromatograph the residue on an Lobar RP-8, size B column (E. Merck) using acetonitrile:water as eluant to give the title compound.

EXAMPLE 3

1-{Nα-(1(S)-Ethoxycarbonyl-3-phenylpropyl]-Nε-[(4-chloro-3-sulfamoyl)benzoyl]-(S)-lysyl}-cis,syn-octahydro-1H-indole-2(S)-carboxylic acid Treat 4.9 g of 1-{Nα[1(S)-ethoxycarbonyl-3-phenylpropyl-(S)-lysyl}-cis,syn-octahydro-1H-indole-2(S) carboxylic acid in 200 ml of tetrahydrofuran and 2.0 g of triethylamine at 0°–5° C. with 2.2 g of 4-chloro-3-sulfamoylbenzoyl chloride and stir the resulting mixture at room temperature. Concentrate the resulting mixture in vacuo and chromatograph the residue on a Lobar RP-8, size B column (E. Merck) using acetonitrile:water as eluant to give the title compound.

EXAMPLE 4

1-{Nα-[1(S)-Ethoxycarbonyl-3-phenylpropyl]-Nε-[(4-chloro-3-sulfamoyl)benzenesulfonyl]-(S)-lysyl}-(S)-proline Substitute 2.17 g of 1-{Nα-[1(S)-ethoxycarbonyl-3-phenylpropyl]-(S)-lysyl}-(S)-proline for the respectively substituted octahydro-1H-indole-2(S)-carboxylic acid in Example 2 to obtain the title compound.

EXAMPLE 5

1-Nα-[1(S)-Ethoxycarbonyl-3-phenylpropyl]-N-[(4-chloro-3-sulfamoyl)benzoyl]-(S)-lysyl-(S)-proline Substitute 2.17 g of 1-{Nα-[1(S)-ethoxycarbonyl-3-phenylpropyl]-(S)-lysyl}-(S)-proline for the respectively substituted octahydro-1H-indole-2(S)-carboxylic acid in Example 3 to obtain the tite compound.

EXAMPLE 6

1-{Nα-[1(S)-Carboxy-3-phenylpropyl]-(S)-lysyl}-cis,-syn-octahydro-1H-indole-2(S)-carboxylic acid To a solution of 1.10 g of 1-{Nα[1(S)-ethoxycarbonyl-3-phenylpropyl]-(S)-lysyl}-cis,syn-octahydro-1H-indole-2(S)-carboxylic acid (prepared as in Example 1) in 100 ml of methanol at 0°–5° C., add 2.0 ml of 2.5 N sodium hydroxide solution and stir at room temperature for 24 hours. Add 20 ml of water, concentrate to one-half volume, and stir 24 hours. Concentrate this solution in vacuo and absorb on AG 50W-X2 (100–200 mesh, hydrogen form, Bio-Rad resin) (50 ml). Place said 50 ml of resin on an additional 300 ml of resin, elute the resin with 1200 ml of water, and then elute with 4% pyridine in water to yield 1-{Nα-[1(S)-carboxy-3-phenylpropyl-(S)-lysyl}-cis,syn-octahydro-1H-indole-2(S)-carboxylic acid, a white solid, m.p. 165°–166° $[\alpha]_D^{26} -8.2$ (ethanol).

EXAMPLE 7

1-{Nα-[1(S)-Carboxy-3-phenylpropyl]-Nε-[(4-chloro-3-sulfamoyl)benzenesulfonyl]-(S)lysyl}-cis,syn-octahydro-1H-indole-2(S)-carboxylic acid Treat 2.45 g of the product from Example 6 with 1.45 g of 4-chloro-3-sulfamoylbenzenesulfonyl chloride as described in Example 2 to give the title compound.

EXAMPLE 8

1-{Nα-[1(S)-Carboxy-3-phenylpropyl]-Nε-[(4-chloro-3-sulfamoyl)benzoyl]-(S)-lysyl}-cis,syn-octahydro-1H-indole-2(S)-carboxylic acid Treat 2.45 g of the product from Example 6 with 1.1 g of 4-chloro-3-sulfamoylbenzoyl chloride as described in Example 3 to give the title compound.

EXAMPLE 9

1-{N-[1(S)-Carboxy-3-phenylpropyl]-S-benzyl-(R)-cysteinyl}-cis,syn-octahydro-1H-indole-2(S)-carboxylic acid, hydrobromide A. Stir 10.5 g of S-benzyl-L-cysteine and 11.0 g of 2-oxo-4-phenylbutyric acid, ethyl ester in 1000 ml of absolute ethanol at room temperature for 24 hours. Add 5.28 g of sodium cyanoborohydride and stir the resulting mixture at room temperature for 48 hours. Concentrate this mixture in vacuo at 30° C. to give a white residue. Suspend the residue in ice-water, add concentrated hydrochloric acid to maintain pH 2–4, and stir this mixture for 1½–2 hours. Absorb this aqueous solution on XAD-2 (Rohm & Haas Co.) resin. Elute the resin with water and then with absolute ethanol. Concentrate the ethanol solution and chromatograph the residue on a column of silica gel using chloroform:isopropanol:7% ammonium hydroxide 1:1:1 (organic layer) to give N-[1(S)-carboethoxy-3-phenylpropyl]-S-benzyl-(R)-cysteine.

B. Treat 4.0 g of the product of part A and 2.6 g of cis,syn-octahydro-1H-indole-2(S)-carboxylic acid, benzyl ester in 10 ml of dimethylformamide at 0° under nitrogen with a solution of 2.75 g of diphenylphosphorylazide in 1.0 g of N-methylmorpholine in 10 ml of dimethylformamide, and stir at room temperature for 18 hours. Pour the reaction solution into water, adjust to pH 8 with 1 N NaOH, and extract with ether. Wash the combined ether layers with aqueous sodium chloride solution, dry the ether layer over magnesium sulfate, filter, and concentrate in vacuo to give a residue. Chromatograph this residue on silica gel (60–200 mesh) using hexane:ethylacetate to give 1-{N-[1(S)-ethoxycarbonyl-3-phenylpropyl]-S-benzyl-(R)-cysteinyl}-cis,syn-octahydro-1H-indole-2-(S)-carboxylic acid, benzyl ester.

C. Stir the product of part B in 50 ml of a 15–20% solution of hydrobromic in acetic acid under nitrogen for 2 hours, then concentrate to dryness under vacuum at room temperature. Triturate the resultant residue with ether to obtain 1-{N-[1(S)-[ethoxycarbonyl-3-phenylpropyl]-S-benzyl-(R)-cysteinyl}-cis,syn-octahydro-1H-indole-2(S)-carboxylic acid, hydrobromide.

D. React 1.5 g of the product from part C in methanol with 3.0 ml of 2.5 N sodium hydroxide at room temperature for 24 hours and concentrate the resulting mixture in vacuo at room temperature. Absorb the residue on AG 50W-X2 (100-200 mesh, hydrogen form, Bio-Rad) resin. Elute the resin with water and then elute with 4% pyridine in water to yield the title compound.

EXAMPLE 10

1-{N-[1(S)-Carboxy-3-phenylpropyl]-(R)-cysteinyl}-cis,syn-octahydro-1H-indole-2(S)-carboxylic acid Treat 1.0 g of product from Example 9 part D with 0.05 g of sodium in 100 ml of liquid ammonia. Evaporate and concentrate the resulting mixture to give the title compound as the sodium salt.

EXAMPLE 11

1-{N-[1(S)-Carboxy-3-phenylpropyl]-S-[3-(6-chloro-3,4-dihydro-7-sulfamoyl-1,2,4-benzothiadiazinyl-1,1-dioxide) methyl]-(R)-cysteinyl}-cis,syn-octahydro-1H-indole-2(S)-carboxylic acid React 0.4 g of the product from Example 10 in 20 ml of dimethylformamide with 0.36 g of 2-bromomethyl-6-chloro-3,4-dihydro-7-sulfamoyl-1,2,4-benzothiadiazine-1,1-dioxide and triethylamine. Concentrate the resulting mixture and chromatograph on an AG 50W-X2 column eluting with 4% pyridine in water to give the title compound.

The compounds of this invention are useful as antihypertensive agents in mammals, including humans, in which the blood pressure has become abnormally elevated. It is believed that the compounds of the present invention act to alleviate or reduce hypertension because they act both as angiotensin converting enzyme inhibitors and as diuretics.

The compounds of the present invention can be combined with pharmaceutical carriers and administered in a variety of well known pharmaceutical forms suitable for oral or parenteral administration to provide compositions useful in the treatment of cardiovascular disorders and particularly mammalian hypertension.

The effective dose ($ED_{50}$) of the compounds of this invention will typically be in the range of about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans, the compounds of this invention may be administered to patients in need of such treatment in a dosage range of 5 to 500 mg per patient generally given several times, thus giving a total daily dose of from 5 to 2000 mg per day.

The composition containing the compounds of this invention will preferably contain from about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

The typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate, polyvinylpyrrolidone, polyvinyl alcohol; stearic acid; alkaline earth metal stearates such as magnesium stearate and calcium stearate, stearic acid vegetable oils such as peanut oil, cottonseed oil, sesame oil, olive oil and corn oil; non-ionic, cationic and anionic surfactants; ethylene glycol polymers; beta-cyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

The following Examples describe in detail compositions that are illustrative of the present invention. It will be apparent to those skilled in the art that many modifications, both of materials and methods, may be practiced without departing from the purpose and intent of this disclosure. In the Examples, the "active ingredient" is 1-{Nα-[1(S)-Ethoxycarbonyl-3-phenylpropyl]-Nϵ-[(4-chloro-3-sulfamoyl)benzensulfonyl]-(S)-lysyl}-cis,-syn- octahydro-1H-indole-2(S)-carboxylic acid.

EXAMPLE 12

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearate into the resulting powder. Encapsulate the mixture into suitably sized two-piece hard gelatin capsules.

EXAMPLE 13

| Tablet | Amount (mg) | |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 14

| Injectable Solution | mg/ml |
|---|---|
| Active ingredient | 5.00 |
| Methyl p-hydroxybenzoate | 0.80 |

-continued

| Injectable Solution | mg/ml |
|---|---|
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

Similarly, substitute other compounds of the present invention (for example, the title compound of Example 3 or the title compound of Example 11) to prepare other compositions of the present invention.

We claim:

1. A compound of the formula $$R^1O-\overset{O}{\underset{\parallel}{C}}-\underset{\underset{R^2}{|}}{\overset{CH_2(S)_n}{C}}-\underset{H}{\overset{|}{N}}-\underset{H}{\overset{Z}{\underset{|}{C}}}-\underset{\parallel}{\overset{O}{C}}-\underset{|}{\overset{CH_2}{N}}-\underset{|}{\overset{A}{CH}}-\underset{|}{\overset{B}{CH}}-\underset{R^3}{\overset{|}{C}}-\overset{O}{\underset{\parallel}{C}}-OR^4$$

I with C$_6$H$_5$–CH$_2$– on first carbon or a pharmaceutically acceptable salts thereof, wherein $R^1$, $R^2$, $R^3$ and $R^4$ are independently selected from hydrogen or lower alkyl; n is 1 or 0; A and B taken together with the carbons to which they are attached form an alkylene ring having six carbon atoms or A and B are hydrogen; and Z is

[structure: H$_2$NSO$_2$– and Cl– substituted benzene with SO$_2$–N(H)–CH(CH$_2$–S–)–N(H) ring]

[structure: H$_2$NSO$_2$– and Cl– substituted benzene with SO$_2$NH(CH$_2$)$_3$–]

or

[structure: H$_2$NSO$_2$– and Cl– substituted benzene with C(=O)–NH(CH$_2$)$_3$–]

2. A compound according to claim 1, wherein n is 0.

3. A compound according to claim 1, wherein $R^3$ is hydrogen.

4. A compound according to claim 1, wherein $R^2$ is hydrogen.

5. A compound according to claim 1, wherein $R^4$ is hydrogen.

6. A compound according to claim 5, wherein n is 0, $R^2$ is hydrogen and $R^3$ is hydrogen.

7. A compound according to claim 1, wherein A and B taken together with the carbon atoms to which they are attached form an alkylene ring having six carbon atoms.

8. A compound according to claim 7, wherein n is 0.

9. A compound according to claim 7, wherein $R^2$ is hydrogen.

10. A compound according to claim 7, wherein $R^3$ is hydrogen.

11. A compound according to claim 7, wherein $R^4$ is hydrogen.

12. A compound according to claim 11, wherein n is 0, $R^2$ is hydrogen and $R^3$ is hydrogen.

13. A compound according to claim 1 or 12 wherein Z is

[structure: H$_2$NSO$_2$– and Cl– substituted benzene with SO$_2$–N(H)–CH(CH$_2$–S–)–N(H) ring]

14. A compound according to claim 1 or 12 wherein Z is

[structure: H$_2$NSO$_2$– and Cl– substituted benzene with SO$_2$NH(CH$_2$)$_3$–]

and

15. A compound according to claim 1 or 12 wherein Z is

[structure: H$_2$NSO$_2$– and Cl– substituted benzene with C(=O)–NH(CH$_2$)$_3$–]

16. A method of treating hypertension in mammals comprising administering to a mammal in need of such treatment an antihypertensive effective amount of a compound according to claim 1.

17. A pharmaceutical composition comprising an antihypertensive effective amount of a compound according to claim 1.

* * * * *